(12) United States Patent
McMurray

(10) Patent No.: US 7,293,433 B1
(45) Date of Patent: Nov. 13, 2007

(54) WARP KNIT FABRICS USEFUL FOR MEDICAL ARTICLES AND METHODS OF MAKING SAME

(75) Inventor: Brian McMurray, Pinehurst, NC (US)

(73) Assignee: Atex Technologies, Inc., Pinebluff, NC (US)

( * ) Notice: Subject to any disclaimer, the term of this patent is extended or adjusted under 35 U.S.C. 154(b) by 0 days.

(21) Appl. No.: 11/222,115

(22) Filed: Sep. 8, 2005

(51) Int. Cl.
*D04B 7/12* (2006.01)
(52) U.S. Cl. .............................. 66/170; 66/195; 66/202
(58) Field of Classification Search .......... 66/190–193, 66/195, 202; 600/37, 16–18; 128/897, 898; 606/15.7; 623/66, 1, 3
See application file for complete search history.

(56) References Cited

U.S. PATENT DOCUMENTS

| | | | |
|---|---|---|---|
| 1,201,803 A | 10/1916 | Chace | |
| 2,992,550 A | 7/1961 | Frith, Jr. | 66/195 |
| 2,996,905 A | 8/1961 | Schiebe | 66/192 |
| 3,118,294 A | 1/1964 | Van Laethem | 66/193 |
| 3,331,221 A | 7/1967 | Lawson, Jr. | 66/170 |
| 3,651,667 A | 3/1972 | Titone | 66/87 |
| 3,653,233 A | 4/1972 | Titone | 66/177 |
| 4,540,398 A | 9/1985 | Barson et al. | 604/1 |
| 4,785,613 A | 11/1988 | Rhode | 56/202 |
| 5,150,706 A | 9/1992 | Cox et al. | 128/400 |
| 5,215,191 A | 6/1993 | Wright | 206/83.5 |
| 5,456,711 A | 10/1995 | Hudson | 623/1 |
| 5,638,703 A | 6/1997 | Callaway | 66/195 |
| 5,702,343 A | 12/1997 | Alferness | 600/37 |
| 5,771,716 A | 6/1998 | Schlussel | 66/195 |
| 5,800,528 A | 9/1998 | Lederman et al. | 623/3 |
| 6,085,754 A | 7/2000 | Alferness et al. | 128/898 |
| 6,375,608 B1 | 4/2002 | Alferness | 600/37 |
| 6,569,082 B1 | 5/2003 | Chin | 600/37 |
| 6,595,912 B2 | 7/2003 | Lau et al. | 600/37 |
| 6,612,978 B2 | 9/2003 | Lau et al. | 600/37 |
| 6,663,558 B2 | 12/2003 | Lau et al. | 600/37 |
| 6,702,732 B1 | 3/2004 | Lau et al. | 600/37 |

OTHER PUBLICATIONS

Capouya et al., Girdling Effect of Nonstimulated Cardiomyoplasty in Left Ventricular Function, 56 Ann. Thorac,surg. 867-881 (1993).

*Primary Examiner*—Danny Worrell
(74) *Attorney, Agent, or Firm*—MacCord Mason PLLC

(57) ABSTRACT

The present invention provides articles useful in medical applications including the treatment of heart diseases, and methods for producing the articles. Embodiments include warp knitted fabrics, both single and multilayer, medical articles and methods of making the same.

41 Claims, 7 Drawing Sheets

WARP KNIT FABRICS USEFUL FOR MEDICAL ARTICLES AND METHODS OF MAKING SAME

CROSS-REFERENCE TO RELATED APPLICATIONS

This non-provisional utility patent application claims the benefit of one or more prior filed provisional applications, a reference to each such prior application is identified as follows: 60/451,479 filed Mar. 3, 2003; and 60/451,327 filed Mar. 3, 2003, each of which is incorporated herein by reference in its entirety.

FIELD OF THE INVENTION

The present invention relates to articles useful in medical applications for restraining organs, limbs and/or other purposes. The present invention also relates to methods for producing the articles. In an embodiment the present invention provides a medical support net adapted to be placed around an organ and a method for producing the medical support net. One type of medical support net is a cardiac support net adapted to be placed around the heart for supporting it. Embodiments of the cardiac support net of the present invention are advantageous for constraining expansion of the heart in a treatment protocol for heart disease.

The present invention also provides alternative fabric embodiments including a biocompatible Raschel warp knit net construction single layer fabric having a plurality of zones of differing stitch length. This single layer fabric may be prepared as a wide open substrate and then cut for specific uses.

BACKGROUND

Restraining and/or constraining a body part, such as an organ, is a useful treatment for many medical conditions For example, it has been proposed to use cardiac support nets in the treatment of heart disease.

Congestive heart failure is a progressive and debilitating illness. The disease may be characterized by a progressive enlargement of the heart. As the heart enlarges, the heart is performing an increasing amount of work in order to pump blood at each heart beat. In time, the heart becomes so enlarged that it cannot adequately supply blood. Further, as the heart enlarges, the internal heart valves cannot adequately close. This impairs the function of the valves and further reduces the heart's ability to supply blood.

Causes of congestive heart failure are not fully known. In certain instances, congestive heart failure may result from viral infections. In such cases, the heart may enlarge to such an extent that the adverse consequences of heart enlargement continue after the viral infection has passed and the disease continues its progressively debilitating course.

Patients suffering from congestive heart failure are fatigued, unable to perform even simple exerting tasks and experience pain and discomfort. These patients are commonly grouped into four classes (i.e., Classes I, II, I and IV as defined by the New York Heart Association—NYHA). In the early stages (e.g., Classes I and II, drug therapy is the commonly prescribed treatment. Drug therapy treats the symptoms of the disease and may slow the progression of the disease. Importantly, there is no cure for congestive heart failure. Even with drug therapy, the disease will progress. Further, the drugs may have adverse side effects.

Presently, the only proven permanent treatment for congestive heart failure is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and may only shortly extend a patient's life. For example, prior to transplant, a Class IV patient may have a life expectancy of 6 months to one-year. Heart transplant may improve the expectancy to about five years.

Unfortunately, an insufficient amount of hearts are available for transplant to meet the needs of congestive heart failure patients. In the United States, in excess of 35,000 transplant candidates compete for only about 2,000 transplants per year. A transplant waiting list is about 8-12 months long on average and frequently a patient may have to wait about 1-2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant for failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprisingly, substantial effort has been made to find alternative treatments for congestive heart failure. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is principally limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

Even though cardiomyoplasty has demonstrated symptomatic improvement in some patients, studies suggest the procedure only minimally improves cardiac performance. The procedure is highly invasive requiring harvesting a patient's muscle and an open chest approach (i.e., sternotomy) to access the heart. Furthermore, the procedure is expensive—specially those using a paced muscle. Such procedures may require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., Reverse Remodeling From Cardiomyoplasty In Human Heart Failure: External Constraint Versus Active Assist, 91 Circulation 2314-2318 (1995). Similarly, cardiac binding is described in Oh et al., The Effects of Prosthetic Cardiac Binding and Adynamic Cardiomyoplasty in a Model of Dilated Cardiomyopathy, 116 J. Thorac. Cardiovasc. Surg. 148-153 (1998), Vaynblat et al., Cardiac Binding in Experimental Heart Failure, 64 Ann. Thorac. Surg. 81-85 (1997) and Capouya et al., Girdling Effect of Nonstimulated Cardiomyoplasty on Left Ventricular Function, 56 Ann. Thorac. Surg. 867-871 (1993).

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle and into the aorta. Such surgeries are expensive. The devices are at risk of mechanical failure and frequently require external power supplies. TAH devices are used as temporary measures while a patient awaits a donor heart for transplant.

U.S. Pat. No. 5,702,343 to Alferness dated Dec. 30, 1997 teaches a jacket to constrain cardiac expansion during diastole. PCT International Publication No. WO 98/29401 published Jul. 9, 1998 teaches a cardiac constraint in the form of surfaces on opposite sides of the heart with the surfaces joined together by a cable through the heart or by an external constraint. U.S. Pat. No. 5,800,528 dated Sep. 1, 1998 teaches a passive girdle to surround a heart. U.S. Pat. No. 6,085,754 dated Jul. 11, 2000 teaches a cardiac constraint device in the form of a knit pouch of open cell fabric.

In an embodiment, the present invention provides an improved cardiac constraint device that provides advantages over the devices disclosed in the aforementioned patents. In addition, the present invention provides a new method for producing a cardiac constraint device.

In addition to cardiac related uses, support nets may be useful in the treatment of other medical conditions. For example, support nets may be useful in restraining other body organs such as the brain, or restraining/constraining body parts such as limbs or the scrotum. Support nets may be also be useful to constrain/restrain organs being prepared for transplant, such as during transportation and/or storage of the organs.

SUMMARY OF THE INVENTION

The present invention provides articles useful in the medical field. Embodiments of the present invention includes articles for the treatment on heart disease and methods for producing the articles.

In a first aspect, the present invention provides embodiments of a warp knitted net structure tubular blank article. The article comprises fully selected Jacquard joining connections integrally knitted into the article connecting two individual layers of fabric at precise points along a curvilinear line. The present invention also provides methods for producing such fabrics.

In an aspect the present invention comprises an integrally formed tubular warp knitted diamond shaped opening net fabric structure blank having a first and a second knit fabric layer that are knitted simultaneously in a parallel spaced relationship and seamlessly connected together at the tube edges by the same yarn knitting the body of the article.

An embodiment of the present invention provides an integrally knitted tubular shaped net structure having first and second parallel knit fabric layers formed on separate parallel spaced front and back needle beds using the same yarn ingredients and knitted identical in fabric construction and yarn runner feed lengths producing a perfect continuously uniform cylindrical shaped tubular blank that can be joined together at one end of the tube by Jacquard selected threads being deflected to knit on both front and back needle beds at predetermined joining points in the design.

An alternate embodiment of the present invention provides a method of producing the aforementioned article but essentially turned sideways approximately 90 degrees and forming an integrally knitted partially closed tubular article that includes one side of the article integrally knitted connecting first and second fabric layers so as to produce a seamless folded edge as the knitted pattern moves from front or said first layer to back or said second layer, while the opposing edge remains open and knitted with a reinforced selvedge.

An article of the present invention may be advantageously used as a jacket or pouch for placement over a heart to restrain congestive heart failure related expansion of the heart. An article of the present invention may also be advantageously used in other medical applications.

In a preferred embodiment of the present invention a method of manufacture is disclosed for producing a jacket or pouch for a medical application, such as for placement over a heart to constrain congestive heart failure related expansion. The jacket may be knitted in one piece, using a biocompatible material, as a pouch having a base end and an apical end with an interior of the pouch sized to receive an organ such as a patient's heart. At the base end, terminating at an edge, the fabric may have a higher fabric density than that of the remainder of the fabric, to facilitate fixation of the jacket to an organ or the heart. An advantage of embodiments of the present invention is that the pouch requires no stitching or sewing since it is knitted in a one-piece format.

Embodiments of the present invention are advantageous for the treatment of heart disease and for treatment of other medical conditions.

Embodiments of medical support nets of the present invention advantageously lack sewn portions, thereby reducing the problems associated with sewing and sewn portions.

Embodiments of the methods of the present invention as set forth hereinabove are advantageous for producing jackets or pouches without the need for sewing.

In another embodiment, the present invention includes a warp knit single layer fabric having a plurality of stitch zones that may be cut and joined to form a pouch.

Another embodiment of the present invention includes a biocompatible Raschel warp knit net construction single layer fabric knitted essentially as a wide open width substrate, having at least two specific differing zones intermittently knitted and alternating from a standard quality and stitch length to a tighter quality with a shorter stitch length. The standard quality and stitch length may be useful for forming the main body of a medical support net such as a heart pouch. The tighter quality with a shorter stitch length may be useful for forming an upper base end of a pouch opening.

The zones may be formed across the full width of the fabric while knitted on the machine, each zone differing in fabric quality and degree of tightness produced by altering of the yarn runner feed lengths and fabric take-up to engineer a net fabric that can be cut and folded over onto itself, either vertically or horizontally, and sewn into a pouch having a base end and an apical end with an interior of the pouch sized for a particular application, such as to receive a patient's heart.

The closing of either the bottom apex end and/or the sides of the pouch may be accomplished by sewing thread techniques. The sewing may be performed along a curvilinear line to produce a pouch shaped for a desired purpose, such as to conform to the human heart.

The base open end comprises the tighter knitted fabric quality zone that provides an area of increased dimensional stability to the open net structure. This zone may be utilized for suturing, for example to suture a cardiac support net embodiment of the present invention to the upper tissue of the heart during surgical installation of the pouch device.

The base open end may include a peripheral edge defining a base opening sized to pass an apex of the item to be constrained, e.g a heart, through the base opening. In embodiments of a cardiac support net of the present invention, the heart may be slipped into the interior of the pouch with the apical end facing the apex of the heart and with the base open end facing toward the upper base of the heart. Similar techniques may be utilized with other organs or body parts.

Embodiments of the present invention are advantageous for producing articles for the treatment of heart disease and for treatment of other medical conditions.

An article of the present invention may be advantageously used to form a jacket or pouch for placement over a heart to restrain congestive heart failure related expansion of the heart. An article of the present invention may also be advantageously used in other medical applications.

DETAILED DESCRIPTION

Figure 1:
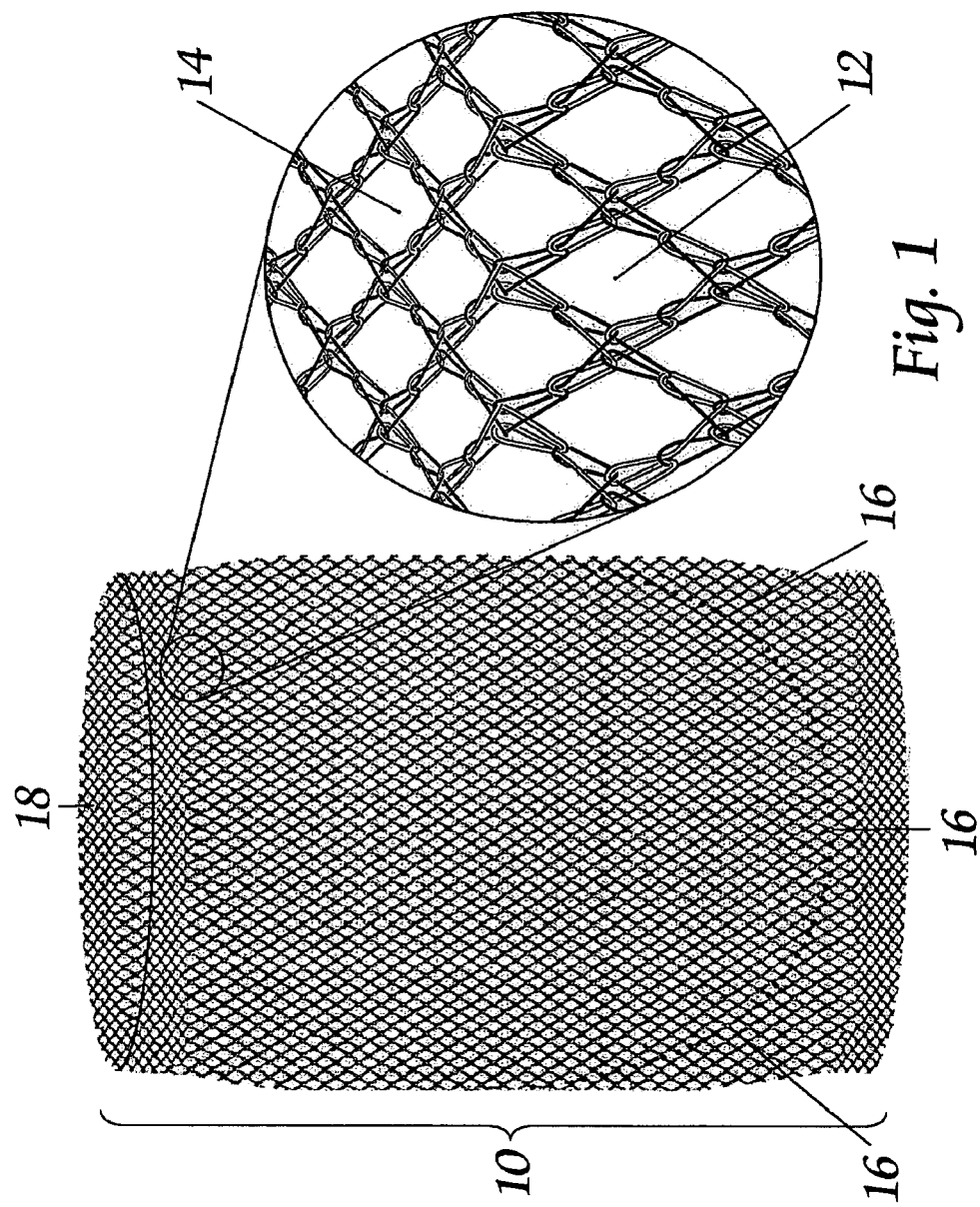
FIG. 1 is a perspective view of a knitted article according to a preferred embodiment of the present invention.

In the drawings and the specification, there have been set forth preferred embodiments of the present invention. Although specific terms are employed, the terms are used in a generic and descriptive sense only and not for the purpose of limitation. It should be understood that the descriptions and drawings, and examples are only illustrative of the present invention. Various alternatives and modifications thereof, can be devised by those skilled in the art without departing from the spirit and scope of the present invention. Accordingly, the present invention is intended to embrace all such alternatives, modifications, and variations that fall within the scope of the appended claims.

For the purposes of this specification, unless otherwise indicated, all numbers expressing quantities of ingredients, reaction conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein, and every number between the end points. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10, as well as all ranges beginning and ending within the end points, e.g. 2 to 9, 3 to 8, 3 to 9, 4 to 7, and finally to each number 1, 2, 3, 4, 5, 6, 7, 8, 9 and 10 contained within the range. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent.

The present invention provides fabrics, both single and double layer knit fabrics, articles useful in medical applications, such as for the treatment of heart disease, and methods for producing such articles.

One embodiment of an article according to the present invention includes a biocompatible fabric knitted as a pouch having a base end and an apical end with an interior of the pouch sized for a particular application such as to receive a patient's heart. In an embodiment, the base end has a peripheral edge defining a base opening sized to pass an apex of the heart through the base opening. The heart is slipped into the interior of the pouch with the apical end facing the apex of the heart and with the base end facing toward a base of the heart. At the base end, terminating at an edge, the fabric has a higher fabric density than that of the remainder of the fabric, to facilitate fixation of the jacket to the heart. The warp knitted article may be uniquely formed utilizing a double needle bar raschel warp knit machine equipped with two full sets of electronically controlled Jacquard guide bars which facilitate the innovation of a method of integrally knitting an engineered tailored shaped pouch article essentially eliminating the need for several subsequent sewing operations, minimizing the number of steps in the manufacturing process.

In a preferred embodiment of the present invention, a warp knitted fabric is provided, more particularly, a double Jacquard—double needle bar raschel warp knitted diamond shaped open net multi-layered fabric pouch-shaped article comprising:

a first discrete diamond shaped net fabric layer,
a second discrete diamond shaped net fabric layer wherein the first and second fabric layers are joined along at least a portion of the end of each layer by integrally knitted joining points thereby forming a substantially tubular sleeve pouch. The first and second discrete fabric layers may be substantially identical mirror images of each other. The first and/or second discrete fabric layer may comprise curved edges to produce a formed pouch.

In another embodiment of the present invention, a biocompatible Raschel warp knit net construction single layer fabric is provided, knitted essentially as a wide open width substrate, having at least two specific differing zones intermittently knitted and alternating from a standard quality and stitch length for the main body of an article to a tighter quality with a shorter stitch length for the upper base end of an article's opening, and is formed across the full width of the fabric while knitted on the machine, each zone differing in fabric quality and degree of tightness produced by altering of the yarn runner feed lengths and fabric take-up to engineer a net fabric that can be cut and folded over onto itself, either vertically or horizontally, and sewn into a pouch having a base end and an apical end with an interior of the pouch sized for a particular application.

Articles of the present invention may be produced with a wide variety of natural and/or synthetic yarns. Preferred yarns are biocompatible. Preferred yarns also comprise multiple filaments.

Suitable yarns for use in embodiments of the present invention include yarns ranging between about 50 and about 100 denier, preferably between about 60 and about 90 denier in size and having a filament count in the range between about 24 and about 42, preferably between about 30 and about 36 denier.

In an embodiment an article of the present invention comprises a continuous multi-filament textured synthetic polymer polyester (polyethyleneterephthalate) yarn.

The fabric layers in an article of the present invention may be knitted using a diamond shaped open net structure comprising a durable four-course repeat Sandfly net stitch construction.

In certain embodiments of the present invention, the uppermost distal open end section of the knitted pouch article may be formed using a tighter, essentially shorter yarn runner feed length without changing knitted stitch construction so as to provide a zone comprised of a more stabilized and denser fabric quality than that of the essentially main body of the pouch article. This portion may serve as a separation point for both cutting into individual pouch articles, as well as a denser reinforced area that may be utilized, for example, for suturing of the upper open end of the pouch article into place during final surgical installation procedures, such as for enveloping the human heart.

In embodiments of the present invention the fabric layers may be integrally knitted together in uninterrupted correct knitting sequence at predetermined, precise Jacquard electronically selected joining points eliminating the need for conventional final stage sewing operations thereby minimizing the number of steps in the manufacturing process.

An article of the present invention may be produced wherein an open edge of the pouch shaped article is provided on one side only of the essentially tubular multi-layer fabric as it is knitted with a portion of the opposite edge integrally and seamlessly knitted in a continuous manner joining the said first discrete fabric layer to the said second discrete fabric layer closing that edge portion and continuously connected to a series of Jacquard selected integrally knitted joining points along a curvilinear line essentially closing the pouch edges continuously up to and including the very edges of the open side of the pouch shaped article as it is progressively knitted in the warp or wale-wise direction.

The fabric layers in an article of the present invention may further comprise supplemental laid-in yarns to further stabilize and reinforce the article and to provide a finished knitted selvedge treatment at the top or uppermost open edges of the pouch shaped article during fabric formation.

Articles of the present invention may be produced in a variety of sizes and configurations for different uses. Details relating to the configurations and sizes of articles of the present invention, and details relating to the use of articles of the present invention, are similar to those set forth in U.S. Pat. No. 6,482,146 to Alferness et al., the disclosure of which is hereby incorporated by reference.

Articles of the present invention are advantageously produced by methods of the present invention.

An aspect of the present invention is a method for producing a fabric pouch shaped article comprising: Jacquard—double needle bar raschel warp knitting first and second discrete diamond shaped net fabric layers and joining the layers along at least one edge by securing integrally within the knit structure. The joining may comprise Jacquard selected joining points along a curvilinear shaped line provided at the bottom most portion of the article as it is progressively knitted in the warp or wale-wise direction.

The method may further comprise laying in supplemental yarns for example to provide a finished knitted selvedge treatment at the top or uppermost open edges of the pouch shaped article during fabric formation.

In embodiments of a method of the present invention the fabric layers may be knitted using a diamond shaped open net structure comprising a durable four-course repeat Sandfly net stitch construction.

In embodiments of a method of the present invention the uppermost distal open end section of the knitted pouch article may be formed using a tighter, essentially shorter yarn runner feed length without changing knitted stitch construction so as to provide a zone comprised of a more stabilized and denser fabric quality than that of the essentially main body of the pouch article, and serving as a separation point for both cutting into individual pouch articles, as well as a denser reinforced area.

The types and sizes of yarns suitable for use in a present invention are set forth above with reference to an article of the present invention.

Embodiments of methods of manufacture according to the present invention do not require a sewing step and therefore eliminate any possible variation in finished product that may have been introduced in the cutting and sewing of previous methods of manufacture. Methods of the present invention may produce a homogenous custom shaped part, with a seam of minimal mass without the need for the use of a sewing thread component.

In another aspect, the present invention provides articles produced by particular processes. In an embodiment, the present invention provides a double Jacquard—double needle bar raschel warp knitted diamond shaped open net multi-layered fabric pouch shaped article formed with a series of knitted courses comprising a first discrete diamond shaped net fabric layer, a second discrete diamond shaped net fabric layer, and produced by a process comprising a Jacquard selected stitching method of joining each of said discrete first and second net fabric layers together, securing integrally within the knit structure, and forming a substantially tubular sleeve pouch that is shaped and closed at one end, and open at the other. The embodiment may further provide that the open end of the essentially tubular multi-layered fabric article is provided at the top uppermost distal end of the article with the closed end of the article comprising Jacquard selected joining points along a curvilinear shaped line provided at the bottom most portion of the article as it is progressively knitted in the warp or wale-wise direction. An open edge of the pouch shaped article may be provided on one side only of the essentially tubular multi-layer fabric as it is knitted with a portion of the opposite edge integrally and seamlessly knitted in a continuous manner joining the said first discrete fabric layer to the said second discrete fabric layer closing that edge portion and is continuously connected to a series of Jacquard selected integrally knitted joining points along a curvilinear line essentially closing the pouch edges continuously up to and including the very edges of the open side of the pouch shaped article as it is progressively knitted in the warp or wale-wise direction. The free and open edges of the pouch shaped article may be further stabilized and reinforced with supplemental laid-in yarns so as to provide a finished knitted selvedge treatment at the top or uppermost open edges of the pouch shaped article during fabric formation. The uppermost distal open end section of the knitted pouch article may be formed using a tighter, essentially shorter yarn runner feed length without changing knitted stitch construction so as to provide a zone comprised of a more stabilized and denser fabric quality than that of the essentially main body of the pouch article, and serving as a separation point for both cutting into individual pouch articles, as well as a denser reinforced area that may be utilized for example for suturing of the upper open end of the pouch article into place during final surgical installation procedures enveloping the human heart. The first and second discrete fabric layers may be integrally knitted together in uninterrupted correct knitting sequence at predetermined, precise Jacquard electronically selected joining points eliminating the need for conventional final stage sewing operations thereby minimizing the number of steps in the manufacturing process.

Embodiments of the present invention may be knitted on a double needle bar warp knitting machine, such as the model RDPJ 6/2N made by Nippon Mayer Ltd., equipped with two jacquard guide bars, one for each needle bed, such as those described in U.S. Pat. No. 5,390,512 dated Feb. 21, 1995.

Each jacquard bar comprises two half-gauge bars with jacquard elements attached that allow individual displacement, by one needle space, of each guide. A patterning device that is electronically connected to the Piezoelectric guides, may be used to control the movement of each guide. When knitting standard fabrics both half-gauge bars are normally shogged by the same number of needle spaces, however in the case of the pouch of the invention the bars are shogged individually. The machine is also equipped with electronically controlled warp let off devices controlling the yarn feed rate of all warp beam sets, and with an electronically controlled take down device to determine the speed of fabric removal from the knitting elements so that one has the ability to change or vary the degree of fabric stitch tightness hence the knitted quality of fabric structure at any desirable position in the repeat of the knitted article.

The fabric construction of choice is a 2 bar net construction (Atlas) popularly known in the trade as Sandfly net and is generally preferred over other net structures for strength and robustness. The net fabric is knitted in mirror image on opposite needle bars. The jacquard bars are fully threaded with a continuous filament synthetic biocompatible yarn, preferably, but not limited to, 70 denier 34 filament textured polyester (polyethyleneterephthalate).

Figure 2:
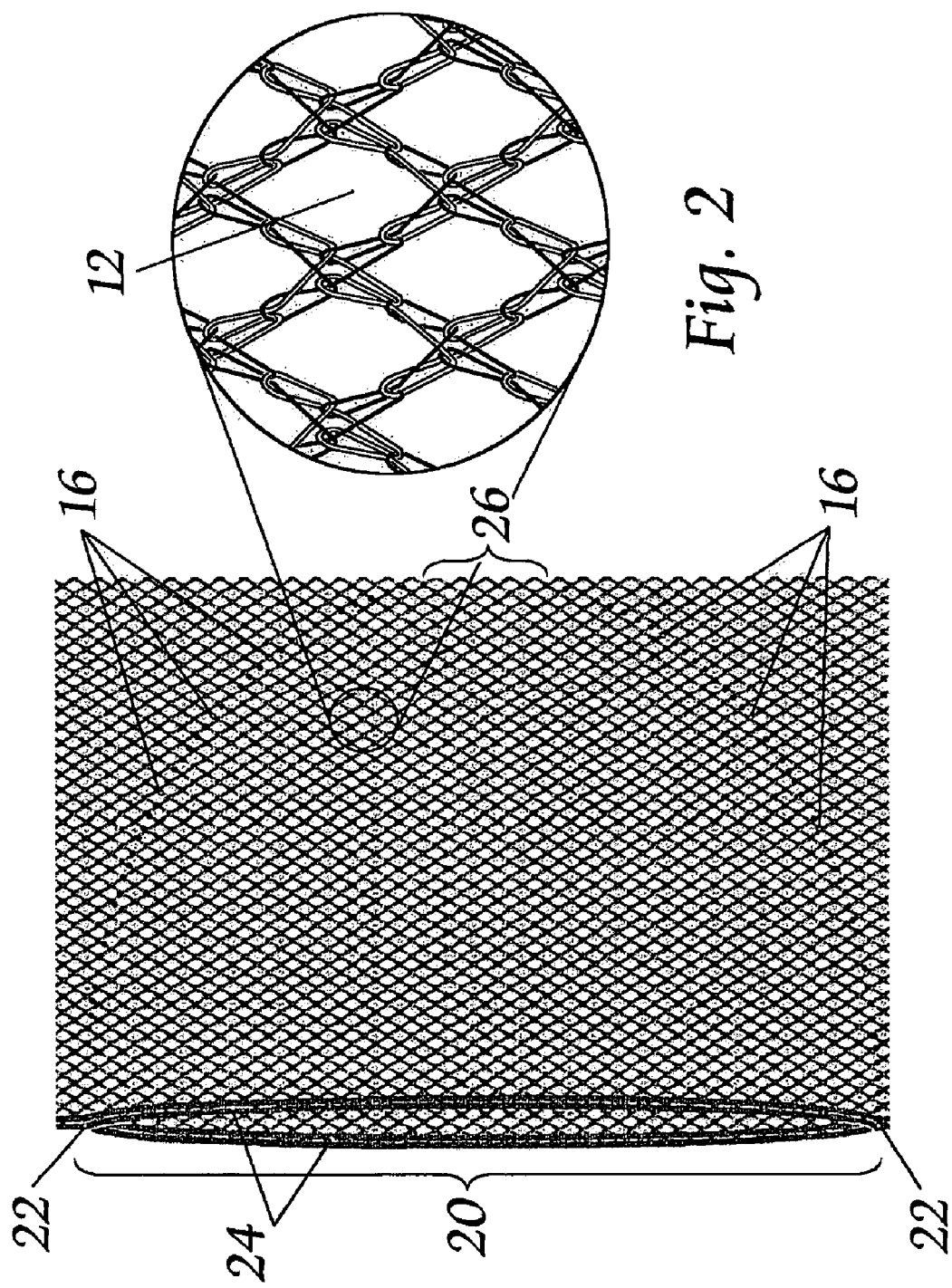
FIG. 2 is a perspective view of knitted article according to an alternate embodiment of the present invention.

At predetermined points, dependent upon the desired final shape of the pouch, guides carrying threads generally knitting on the front needle bar are deflected using the jacquard elements and made to knit on the back needle bar. Also guides carrying threads generally knitting on the back needle bar are deflected using the jacquard elements and made to knit on the front needle bar. This action creates a join from the front fabric layer to the back fabric layer, forming an integrally knitted seam, at Jacquard pattern selected points in the design and are shown as join points 16 as illustrated in FIG. 1 and FIG. 2 An integrally knitted seam is highly advantageous as opposed to a normally required sewn seam using a biocompatible sewing thread, essentially knitting one fabric to the other in perfect sequential order of stitch pattern notation according to the four course repeat of the Sandfly diamond shaped net structure. The resultant merged yarns from the first layer of net fabric into the second layer of net fabric become one homogenous unified net at that instance, and therefore the need for a separate sewing or tacking operation during the manufacture of the finished article is eliminated, reducing the number of steps in the final manufacturing process and eliminating the need for additional sewing materials and the associated variables and potential for human error that are inherent in such operations. At the beginning of the pouch pattern for a predetermined number of courses the runner lengths and courses per inch are changed by altering the rate at which the warp let off device and take down device operate. This changes the fabric density for the predetermined number of courses. In this instance the yarn inch feed rate is shortened essentially tightening the structure, making each individual stitch length shorter, and increasing the density and dimensional stability of that zone of fabric knitted.

Referring now to the drawings, FIG. 1 illustrates a perspective view of a preferred article produced essentially as a tubular shaped warp knitted net structure, shown generally at 10, according to the present invention. According to the predetermined design and part size required, a length of tubular net fabric is first knitted beginning at the bottom of the tube with a defined number of courses using a specific tighter yarn feed-in requirement resulting in a relatively stronger, more stabilized zone of a relatively higher fabric density and number of stitches per square inch than the body of the article, shown as 14. This area provides a marker reference for cutting in order to separate the individual articles out from a continuous tubular length as it comes off the fabric take-up rolls of the knitting machine. It also serves as to provide an additional upper area at the top of the article shown as 18 for suturing the jacket to the upper heart tissue as the final product is surgically installed in the patient. The tighter and smaller hole size area 14 is of a tighter and more stabilized knit structure than the body of the article shown as 12 of the article 10. The main body of the tubular article is then knitted using a longer yarn feed runner length to essentially loosen up the diamond net structure to a longer knit quality throughout the knitting of the article until the desired distance is achieved before again shortening the yarn runner feed lengths in order to knit a zone 18 at the upper open top end of the tubular article.

Figure 3:
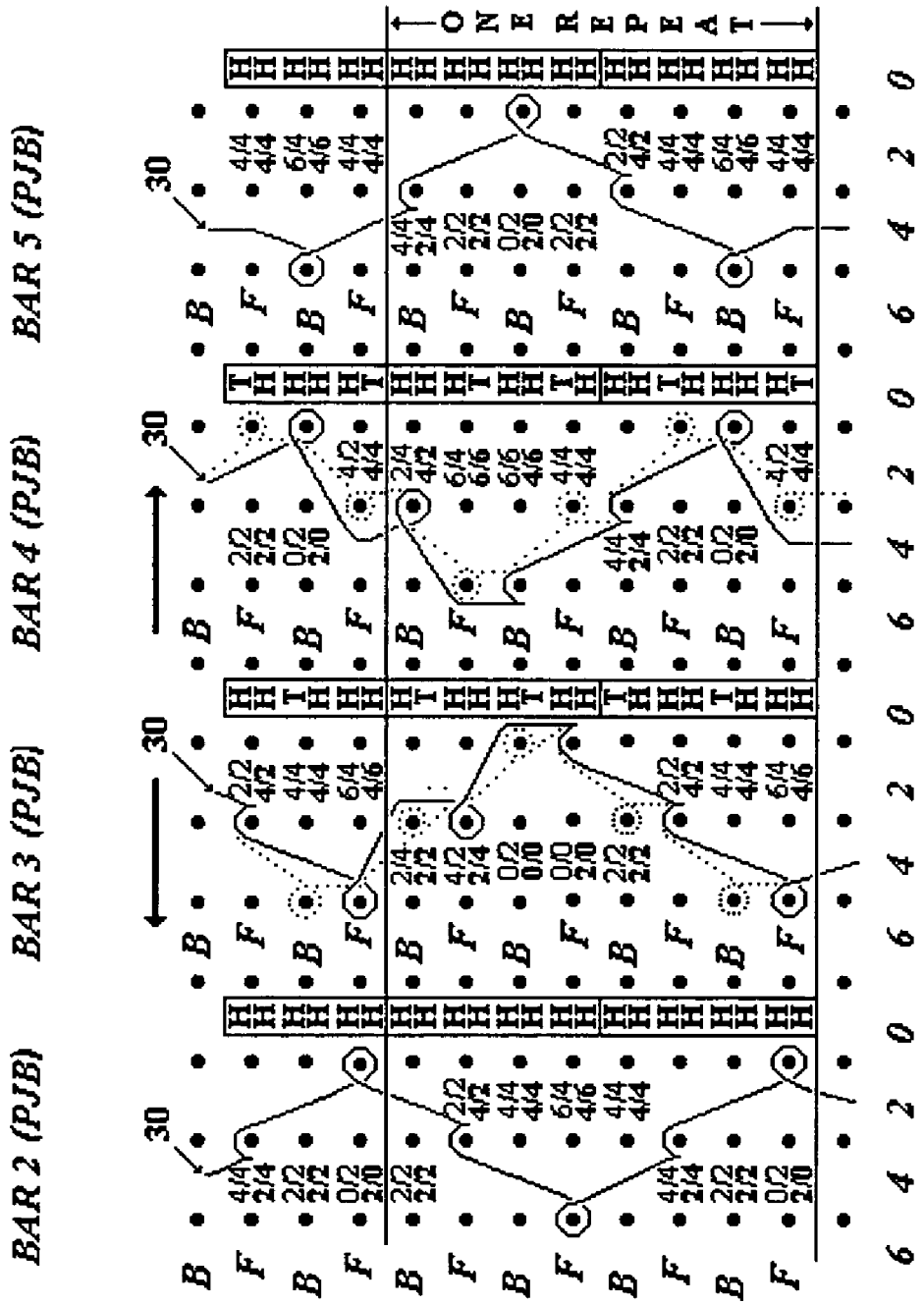
FIG. 3 illustrates an exemplary warp knitting sequence and method of knitting for producing the preferred embodiment as illustrated in FIG. 1.
Figure 4:
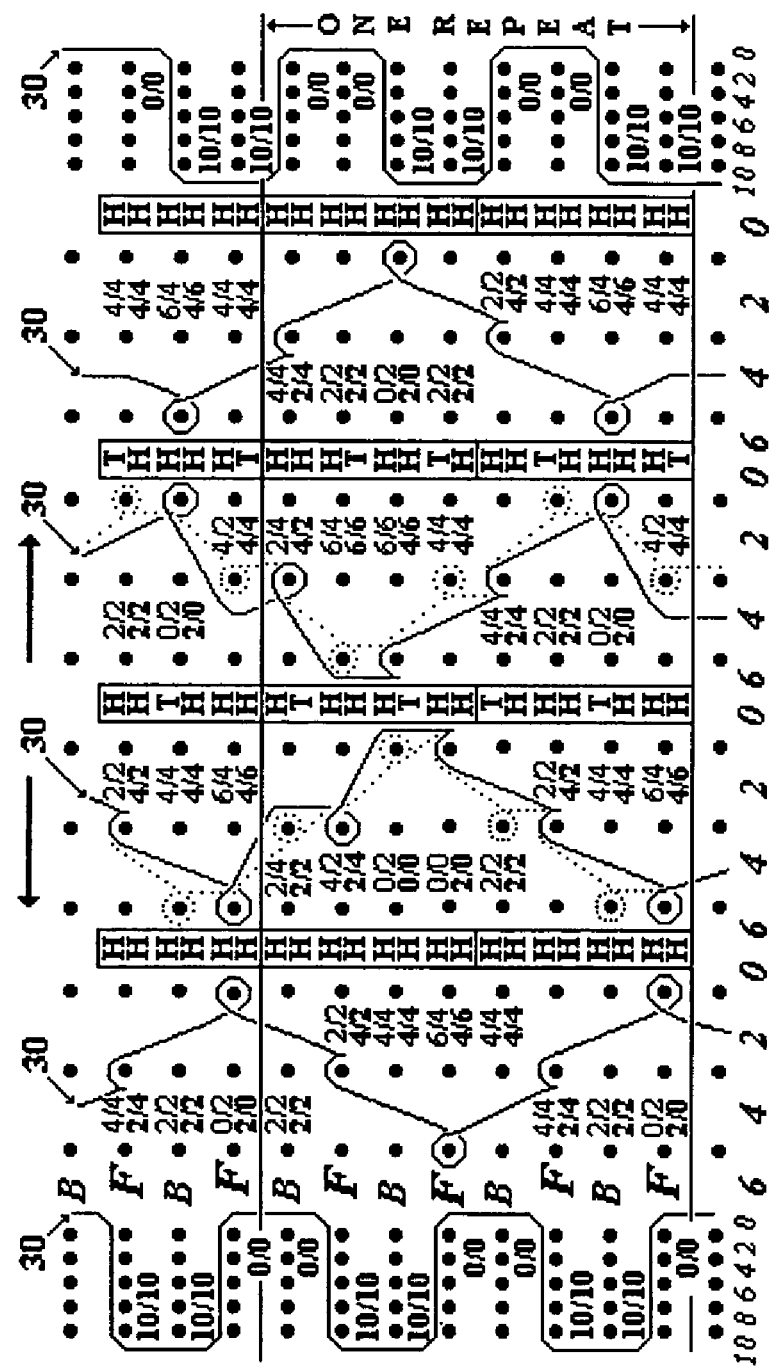
FIG. 4 illustrates an exemplary warp knitting sequence and method of knitting for producing the alternate embodiment as illustrated in FIG. 2.

One end of the tubular will remain open, shown as 18, whilst the other end of the tubular knitted blank will be knitted closed and joined together at sequential points along a curvilinear line illustrated as 16. The technique and method of knitting said fabric layer joining points using Jacquard Piezoelectric yarn deflection is illustrated in FIG. 3 and FIG. 4, according to the present invention. This integrally knitted seam 16 also serves as a guide for the final cutting away of excess fabric as the heart jacket device approaches the final stages of completion including scouring and heat molding to final shape.

FIG. 2 illustrates an alternate embodiment of the present invention shown generally as 20. FIG. 2 provides an illustration of a method of producing the aforementioned preferred article as shown in FIG. 1, but essentially turned sideways 90 degrees and is forming an integrally knitted partially closed tubular article that essentially has one side of the article integrally knitted connecting first and second fabric layers so as to produce a seamless folded edge as the knitted pattern moves from front or said first layer to back or said second layer, shown as 26 of FIG. 2. The side of the article opposite to the knitted seamless fold 26 shall remain essentially open and independent first and second separate fabric layers, shown as 24 of FIG. 2. Further, the free edges of the first and second fabric layers may be reinforced with the same yarn size and type as used throughout the article but utilizing a laid-in stitch method that differs from the knit stitch method used in forming the diamond shaped net structure of the body. This technique will serve to reinforce the open edges 24 that will become the upper finished top edge of the final heart jacket once the two individual front and back fabric layers are joined together through Piezoelectric Jacquard selection of yarns at joining points 22, shown in FIG. 2. Continuing from the points of connection at 22, joining points 16 will connect the first front fabric layer and second back fabric layer through Piezoelectric Jacquard selection of yarns deflected to knit on both the front and back needle beds at precise connecting points along a curvilinear line according to the article pattern design shape 16 as illustrated in FIG. 2.

The method of producing the fabric blank article 10 of FIG. 1 will therefore be understood and is best described in FIG. 3 according to the respective stitch construction. FIG. 3 illustrates the exemplary design pattern repeat warp knit stitch notation and lap diagram required to knit manufacture exemplary tubular article 10. Knitting this embodiment requires a double needle bar machine equipped with two individual sets of compound Jacquard guide bars, one for each needle bar as is the particular machine model RDPJ 6/2N made by Nippon Mayer Ltd. of Fukui-city, Japan, a subsidiary of Karl Mayer Textilmaschinenfabrik GmbH of Obertshausen, Germany. Again referring to FIG. 3, the knitted article is fully threaded into both sets of compound Jacquard Bars (PJB 2 & PJB 3) and (PJB 4 and PJB 5) in a solid arrangement throughout using preferred yarn designated as 70 denier, 34 filament textured polyester illustrated as yarn 30 into each of the four individual Jacquard guide bars. PJB Bar 2 is knitting a four-course repeat or essentially one side of the atlas diamond net and only knits on the alternate front needle bed courses designated as F, missing all needles of back needle bed B. Therefore, when knitting a four-course stitch pattern repeat on one needle bar (front) of a double needle bar machine it is required to also program the machine so as to alternately miss the other (back) needle bar requiring eight courses in the repeat sequence of the basic stitch in order to complete four courses on each needle bar. In FIG. 3 for example, PJB Bar 2 knits and overlaps only needles on the front needle bar (F): 2/0, 2/4, 4/6, 4/2. No overlapping of needles with yarn from PJB2 occurs on needles of the back needle bar (B). All overlapping of yarns from PJB Bar 2 on the back bar needles is totally avoided by missing the back bar altogether as 2/2, 4/4, 4/4, 2/2. Yarn 30 fully threaded in a solid arrangement repeatedly to the width of the article into PJB Bar 3 yarn forms the other half of the atlas diamond net provided by PJB 2 and only knits on the alternate front needle bed F, missing all needles of back needle bar B. First diamond net fabric layer then is essentially formed on the front needle bar (F) using PJB Bar 2 and PJB Bar 3. Likewise, second and distinct diamond net fabric layer is formed on the back needle bar (B) using PJB Bar 4 and PJB Bar 5 with each of these bars forming essentially one side of the diamond net structure as integrally knitted together. According to the overall design of the knitted article, the Jacquard selection for yarn guide deflection is then effected only on PJB Bar 3 and PJB Bar 4, while using PJB Bar 2 and PJB Bar 5 essentially as standard cam driven guide bars not requiring any Piezoelectric Jacquard selected deflection and therefore designated with an (H) instruction on every link of every course of the course full pattern repeat of the net. The German term "Hoch", meaning "high" signifying a "no" to deflection action, comes from the earlier original mechanical action Jacquard controls whereby a lifted spring-loaded displacement pin in each guide of the Jacquard guide bar is lifted high and held out of action therefore preventing the deflection of the guide by one needle space and for illustration purposes is therefore designated as (H) for "Hoch". (The Piezoelectric yarn guide innovation replaced the old mechanical control Jacquard many modern machine models built in recent years by Karl Mayer Textilmaschinen GmbH of Obertshausen, Germany, thereby increasing speeds of deflection through electronic signal ceramic deflection technology and subsequently increased machine knitting speeds). Integral knitting and combining of first diamond net fabric layer formed on the front needle bar with second fabric diamond net fabric layer formed on the back needle bar at the select points such as the seamless edges closing tube and the specific joining points tacking the tube together along the curvilinear line are accomplished by Jacquard Piezoelectric signal instructions to the PJB (Piezoelectric Jacquard Bar) designated as (T). (T) signifying the German word "Tief" meaning "deep" or a "yes" instruction to deflection by allowing the old mechanical spring loaded pin to drop and push the sliding movable Jacquard guide laterally by one needle space. The deflection instruction of "Tief" is now accomplished with the faster electronic signal device referred to as a Piezoelectric bending transducer to be driven by electric pulse generators that apply electric pulses to selected guides at precise times according to the computer program pattern design. The carefully programmed stitch points are accomplished by deflection of the PJB Bar 3 and PJB Bar 4 yarns so they overlap the needles of both front (F) and back (B) needle bars creating the exact same four-course repeat net stitch sequence on both, resulting in the joining of the two net fabric layers as one fabric of uniform construction at those selected locations. In the case of the very edge of the closure of the tube on both sides, the join is made using Jacquard deflection to seamlessly connect each of first front fabric layer and second back fabric layer in a perfect connection resulting in a single layer continuous and technically correct seamless join of face to back layers and forming a flawless diamond mesh tube.

Now referring to FIG. 4, as depicted is the knitting technique used to make the alternately preferred article as illustrated in FIG. 2. The knitting sequence of the four-course Sandfly diamond net as illustrated and executed in FIG. 3 and used to create the exemplary article illustrated in FIG. 1, is also used to construct the article as in FIG. 2 with the exception that the additional available guide bars of the machine numbered Bar 1 and Bar 6 are used for the purpose of laying-in just two ends of yarn 30, threaded 1-in, 5-out into Bar 1 and two ends into Bar 6 on the one side of the article 20 that is essentially left open and features a laid-in selvedge 22 on each of the first front needle bar diamond net fabric layers and the second back needle bar diamond net fabric layers. The laid-in yarn of Bar 1 is programmed and directed to place the yarn on the needles of the front bar (F) only in a laid-in method of 0/0, 10/10, 0/0, 10/10. Any overlapping of back needle bar needles or lay-in of yarn onto the back needle bar (B) is therefore avoided by missing as 10/10, 0/0, 10/10, 0/0 on the back needle bar courses. Hence, the complete sequential order of the numerical instructions for one repeat of the basic diamond and selvedge treatment from Bar 1 is: 0/0, 10/10, 10/10, 0/0, 0/0, 10/10, 10/10, 0/0

The two selvedge ends threaded 1-in, 5-out on the backmost guide Bar 6 essentially lay-in on the needles of the back bar (B) only as 10/10, 0/0, 10/10, 0/0, avoiding and missing the front needle bar (F) by programming movements as 10/10, 0/0, 10/10, 0/0. Hence, the complete sequential order of the numerical instructions for one repeat of the basic diamond and selvedge treatment from Bar 6 is: 10/10, 10/10, 0/0, 0/0, 10/10, 10/10, 0/0, 0/0.

Figure 5:
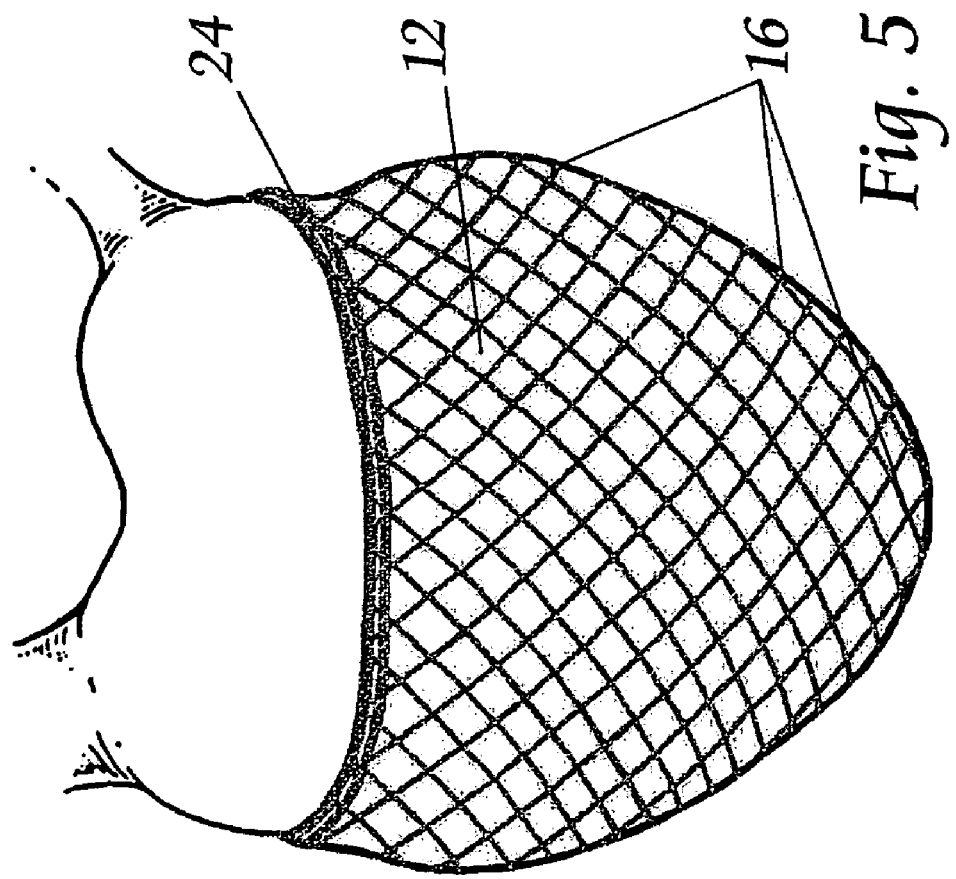
FIG. 5 shows an exemplary application of the present invention as a knitted jacket sized to envelope the human heart.

The selvedge reinforced edges 24 of article 20 as depicted in FIG. 2 are integrally knitted and tacked together at points 22 by selected Piezoelectric Jacquard deflection according to the design of the article as illustrated in FIG. 2. Joining points 16 following a curvilinear line connect the individual fabric layers from the front needle bar (F) and the back needle bar (B) and essentially shape the article, defining the cutting line for final manufacturing steps. The excess fabric is cut and removed from outside of the line 16 of successive joining points. The resulting article as formed and illustrated in FIG. 2 is depicted in FIG. 5 in the application of an embodiment of the invention as it is applied enveloping a human heart for support.

In addition to the foregoing, the present invention also provides fabrics useful for producing articles useful in medical applications, such as for the treatment of heart disease, and methods for producing such articles.

Figure 6:
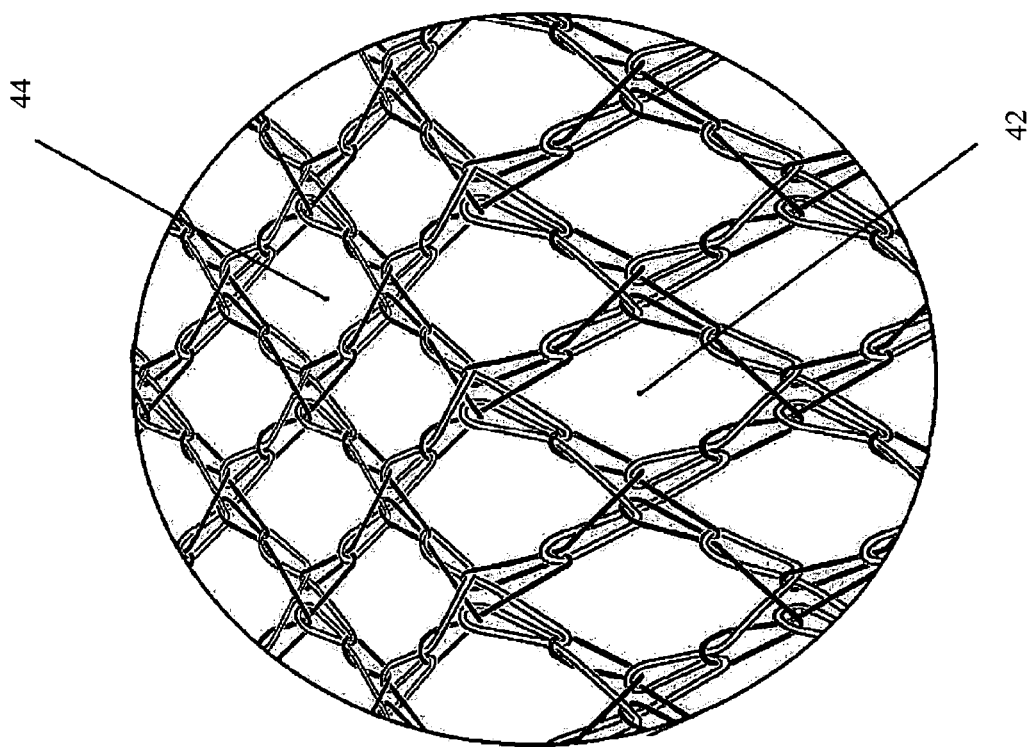
FIG. 6 shows a section of a knitted fabric according to one embodiment of the present invention.
Figure 7:
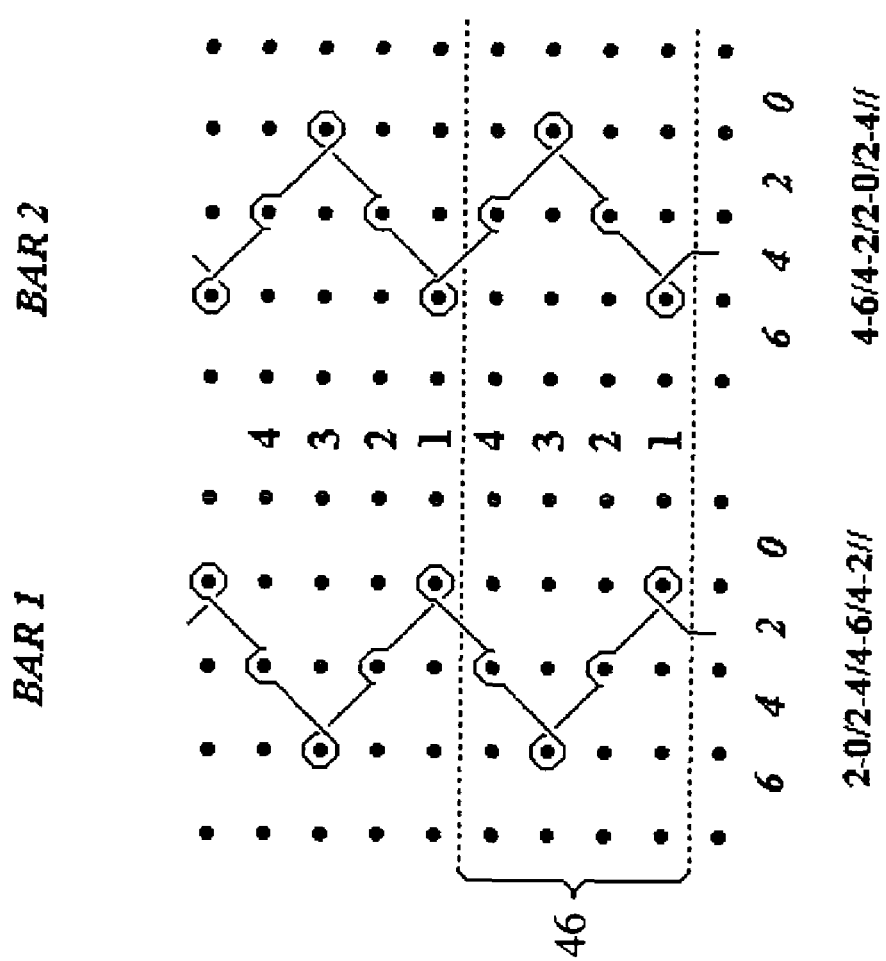
FIG. 7 an exemplary warp knitting sequence and method of knitting for producing the alternative single layer embodiment of FIG. 6.

As illustrated in FIGS. 6 and 7, an embodiment of the present invention includes a biocompatible Raschel warp knit net construction single layer fabric (shown in FIG. 6) knitted essentially as a wide open width substrate, having at least two specific differing zones 42, 44 intermittently knitted and alternating from a standard quality having a first number of meshes per square inch and a first stitch length to a tighter quality having a greater number of meshes per square inch with a shorter stitch length. FIG. 7 shows a "Sandfly Net" atlas basic lap diagram where BAR 1 is half threaded 1-in, 1-out and BAR 2 is also half threaded 1-in, 1-out, with one repeat being shown 46.

In an embodiment, the present invention provides a raschel warp knitted diamond shaped open net fabric comprising a plurality of stitch zones.

Fabrics of the present invention may be produced with a wide variety of natural and/or synthetic yarns. Preferred yarns are biocompatible. Preferred yarns also comprise multiple filaments.

Suitable yarns for use in embodiments of the present invention include yarns ranging between about 50 and about 100 denier, preferably between about 60 and about 90 denier in size and having a filament count in the range between about 24 and about 42, preferably between about 30 and about 36.

In an embodiment an article of the present invention comprises a continuous multi-filament textured synthetic polymer polyester (polyethyleneterephthalate) yarn.

The fabric in an article of the present invention may be knitted using a diamond shaped open net structure comprising a durable four-course repeat Sandfly net stitch construction.

In embodiments of the present invention a first stitch zone may be formed utilizing conventional techniques and a second stitch zone may be formed using a tighter, essentially shorter yarn runner feed length without changing knitted stitch construction so as to provide a zone comprised of a more stabilized and denser fabric quality. This portion may serve as a separation point for both cutting into individual pouch articles, as well as a denser reinforced area that may be utilized, for example, for suturing of the upper open end of the pouch article into place during final surgical installation procedures, such as for enveloping the human heart.

Fabrics of the present invention may further comprise supplemental laid-in yarns to further stabilize and reinforce articles produced from the fabric for example to provide a finished knitted selvedge treatment at the top or uppermost open edges of a pouch shaped article produced from the fabric.

Embodiments of the present invention may be knitted on a machine equipped with electronically controlled warp let off devices controlling the yarn feed rate of all warp beam sets, and with an electronically controlled take down device to determine the speed of fabric removal from the knitting elements so that one has the ability to change or vary the degree of fabric stitch tightness hence the knitted quality of fabric structure at any desirable position in the repeat of the knitted article.

The fabric construction of choice comprises a 2 bar net construction (Atlas) popularly known in the trade as Sandfly net and is generally preferred over other net structures for strength and robustness. The guide bars are half threaded (1 in 1 out) with a continuous filament synthetic biocompatible yarn, preferably, but not limited to, 70 denier 34 filament textured polyester (polyethyleneterephthalate).

Details relating to particular knitting techniques and other methods of producing the fabrics of the present invention are set forth hereinabove.

Although the present invention has been described with reference to particular embodiments, those of ordinary skill in the art will appreciate that the system of the present invention may be implemented in other ways and embodiments. Accordingly, the description herein should not be read as limiting the present invention as other embodiments also fall within the scope of the present invention.

Although the present invention has been described with reference to particular embodiments, those of ordinary skill in the art will appreciate that the system of the present invention may be implemented in other ways and embodiments. Accordingly, the description herein should not be read as limiting the present invention as other embodiments also fall within the scope of the present invention. In addition, although embodiments of the present invention have been described with reference to cardiac support nets, the present invention includes other embodiments advantageous for other uses. Certain modifications and improvements will occur to those skilled in the art upon a reading of the foregoing description. By way of example, other synthetic polymeric yarn materials may be used, provided that the yarn functions appropriately for medical applications for which the fabric is applied. All modifications and improvements have been deleted herein for the sake of conciseness and readability but are properly within the scope of the following claims.

What is claimed is:

1. An article for medical applications comprising:
a double Jacquard—double needle bar Raschel warp knitted diamond-shaped open net multilayered fabric pouch, wherein the multilayer fabric pouch comprises:
a first discrete diamond shaped net fabric layer,
a second discrete diamond shaped net fabric layer,
wherein the first and second net fabric layers together are integrally secured using Jacquard knit stitches.

2. The article of claim 1 wherein the pouch comprises open and closed ends wherein, the open end comprises Jacquard selected joining points along a curvilinear shaped line.

3. The article of claim 2 further comprising supplemental laid-in yarns.

4. The article of claim 1 wherein the fabric layers comprise a continuous multi-filament textured synthetic polymer polyester yarn.

5. The article of claim 1 wherein the fabric layers comprise a continuous multifilament textured polyester yarn in a range of between about 60 and about 90 denier in size, and a filament count in a range of between about 30 and about 36.

6. The article of claim 1 wherein the fabric layers comprise a diamond shaped open net structure comprising a durable four-course repeat Sandfly net stitch construction.

7. The article of claim 1 wherein an uppermost distal open end section of the knitted pouch article comprises a shorter yarn runner so as to provide a zone comprised of a more stabilized and denser fabric than the main body of the pouch article.

8. The article of claim 1 wherein the first and second discrete fabric layers are integrally knitted together in uninterrupted correct knitting sequence at predetermined or precise Jacquard electronically selected joining points.

9. An isolated heart surrounded by an article of claim 1.

10. A method of knitting a double Jacquard—double needle bar Raschel warp knitted diamond shaped open net multi-layered fabric pouch shaped article formed with a series of knitted courses comprising the steps of:
knitting a first discrete diamond shaped net fabric layer and a second discrete diamond shaped net fabric layer;
joining the layers; and
forming an essentially tubular sleeve pouch that is shaped and closed at one end, and open at the other.

11. The method of claim 10, wherein the joining step further includes joining the layers utilizing a Jacquard stitching method of joining each of said discrete first and second net fabric layers together, securing integrally within the knit structure, and forming an essentially tubular sleeve pouch that is shaped and closed at one end, and open at the other.

12. The method of claim 10 wherein, an open end of the essentially tubular multi-layered fabric article is provided at the top uppermost distal end of the article with the closed end of the article comprising Jacquard selected joining points along a curvilinear shaped line provided at the bottom most portion of the article as it is progressively knitted in the warp or wale-wise direction.

13. A method of knitting a multi-layered fabric pouch article according to claim 10 wherein, an open edge of the pouch shaped article is provided on one side only of the essentially tubular multi-layer fabric as it is knitted with a portion of the opposite edge integrally and seamlessly knitted in a continuous manner joining the said first discrete fabric layer to the said second discrete fabric layer closing that edge portion and is continuously connected to a series of Jacquard selected integrally knitted joining points along a curvilinear line essentially closing the pouch edges continuously up to and including the edges of the open side of the pouch shaped article as it is progressively knitted in the warp or wale-wise direction.

14. A method of knitting a multi-layered fabric pouch article according to claim 10 wherein, the free and open edges of the pouch shaped article are further stabilized and reinforced with supplemental laid-in yarns so as to provide a finished knitted selvedge treatment at the top or uppermost open edges of the pouch shaped article during fabric formation.

15. A method of knitting according to claim 10 wherein the series of knitted courses comprise a continuous multifilament textured synthetic polymer polyester yarn.

16. A method of knitting according to claim 10 wherein, each of said first and second discrete warp knitted fabric layers comprise continuous multifilament textured polyester yarn in a range of between about 60 and about 90 denier in size, and a filament count in a range of between about 30 and about 36.

17. A method of knitting according to claim 10 wherein, each of the said first discrete and second discrete fabric layers are knitted using a diamond shaped open net structure comprising a durable four-course repeat Sandfly net stitch construction.

18. A method of knitting a fabric according to claim 10 wherein, the uppermost distal open end section of the knitted pouch article is formed using a tighter, essentially shorter yarn runner feed length without changing knitted stitch construction so as to provide a zone comprised of a more stabilized and denser fabric quality than that of the essentially main body of the pouch article, and serving as a separation point for both cutting into individual pouch articles, as well as a denser reinforced area.

19. A method of knitting the fabric according to claim 10 wherein the said first and second discrete fabric layers are integrally knitted together in uninterrupted correct knitting sequence at precise Jacquard electronically selected joining points eliminating the need for conventional final stage sewing operations.

20. A method for treating heart disease comprising surrounding a heart with an article of claim 1.

21. A double Jacquard—double needle bar raschel warp knitted diamond shaped open net multi-layered fabric pouch sized, shaped and constructed for use as a medical support net structure, wherein the multi-layer fabric pouch comprises: a first discrete diamond shaped net fabric layer, second discrete diamond shaped net fabric layer, wherein the first and second net fabric layers together are integrally secured using Jacquard knit stitches.

22. The fabric of claim 21 wherein the fabric layers comprise a continuous multi-filament textured synthetic polymer polyester yarn.

23. The fabric of claim 21 wherein the fabric layers comprise a continuous multifilament textured polyester yarn in a range between about 60 to about 90 denier in size, and a filament count in a range between about 30 to about 36.

24. The fabric of claim 21 wherein the fabric layers comprise a diamond shaped open net stricture comprising a durable four-course repeat Sandfly net stitch construction.

25. The fabric of claim 21 wherein an uppermost distal open end section of the knitted pouch article comprises a shorter yarn runner so as to provide a zone comprised of a more stabilized and denser fabric than the main body of the pouch article.

26. The fabric of claim 21 wherein the first and second discrete fabric layers are integrally knitted together in uninterrupted correct knitting sequence at precise Jacquard electronically selected joining points.

27. The fabric of claim 21 wherein the multilayer fabric pouch is sized, shaped and constructed to support a heart.

28. The fabric of claim 21 wherein the pouch comprises open and closed ends wherein, the open end comprises Jacquard selected joining points along a curvilinear shaped line.

29. The fabric of claim 21 further comprising supplemental laid-in yarns.

30. A biocompatible Raschel warp knit net construction single layer fabric comprising a plurality of differing zones intermittently knitted and alternating from a standard quality having a first number of meshes per square inch and a first stitch length to a tighter quality having a greater number of meshes per square inch with a shorter stitch length, wherein the fabric comprises a diamond shaped open net structure comprising a durable four-course repeat Sandfly net stitch construction.

31. The fabric of claim 30 further comprising: supplemental laid-in yarns.

32. The fabric of claim 31 formed from a continuous multi-filament textured synthetic polymer polyester yarn.

33. The fabric of claim 30 formed from a continuous multifilament textured polyester yarn in a range of between about 60 and about 90 denier in size, and a filament count in a range of between about 30 and about 36.

34. A medical article formed from the fabric of claim 30.

35. A method of making the fabric of claim 30 comprising the steps of: knitting a single layer fabric in a Raschel warp knit net construction, wherein the fabric is capable of being used for forming a biocompatible medical construction therewith.

36. The method of claim 35, wherein the single layer fabric is a biocompatible Raschel warp knit net construction single layer fabric comprising a plurality of differing zones intermittently knitted and alternating from a standard quality having a first number of meshes per square inch and a first stitch length to a tighter quality having a greater number of meshes per square inch with a shorter stitch length.

37. The method of claim 36 further including the step of providing supplemental laid-in yarns.

38. The method of claim 37 wherein the knitting step further includes forming the fabric from a continuous multi-filament textured synthetic polymer polyester yarn.

39. The method of claim 35 formed from a continuous multifilament textured polyester yarn in a range between about 60 to about 90 denier in size, and a filament count in a range between about 30 to about 36.

40. The method of claim 35 wherein the fabric comprises a diamond shaped open net structure comprising a durable four-course repeat Sandfly net stitch construction.

41. A method of forming a medical article comprising the steps of: knitting a biocompatible single layer fabric having a diamond shaped open net structure comprising a durable four-course repeat Sandfly net stitch construction and forming the medical article therewith.

* * * * *

UNITED STATES PATENT AND TRADEMARK OFFICE
CERTIFICATE OF CORRECTION

| | | |
|---|---|---|
| PATENT NO. | : 7,293,433 B1 | Page 1 of 1 |
| APPLICATION NO. | : 11/222115 | |
| DATED | : November 13, 2007 | |
| INVENTOR(S) | : Brian McMurray | |

It is certified that error appears in the above-identified patent and that said Letters Patent is hereby corrected as shown below:

Title Page, Insert:

(63) --This application is a continuation of Application Serial No. 10/791,058 filed March 2, 2004, now abandoned, which claimed priority of Provisional Application Number 60/451,479 filed March 3, 2003, and Provisional Application Number 60/451,327 filed March 3, 2003.--

Title Page, Item (56) Other Publications:
The following non-patent references were omitted from the face of the patent:

"Kass et al., Reverse Remodeling From Cardiomyoplasty in Human Heart Failure: External Constraint Versus Active Assist, 91 Circulation 2314-2318 (1995)

Oh et al., The Effects of Prosthetic Cardiac Binding and Adynamic Cardiomyoplasty in a Model of Dilated Cardiomyopathy, 116 J. Thorac. Cardiovasc. Surg. 148-153 (1998)

Vaynblat et al., Cardiac Binding in Experimental Heart Failure, 64 Ann. Thorac. Surg. 81-85 (1997)"

Column 1, Line 38, "conditionsFor" should read --conditions. For--

Column 1, Line 60, should read --Classes I, II, III and IV--

Column 17, Line 12, "stricture" should be --structure--

Signed and Sealed this

Eighteenth Day of March, 2008

JON W. DUDAS
*Director of the United States Patent and Trademark Office*